United States Patent
Dastillung et al.

(10) Patent No.: US 10,654,763 B2
(45) Date of Patent: May 19, 2020

(54) PROCESS FOR PRODUCING BUTADIENE FROM ETHANOL INTEGRATED WITH EXTRACTIVE DISTILLATION

(71) Applicants: IFP Energies nouvelles, Rueil-Malmaison (FR); Compagnie Generale des Etablissements Michelin, Clermont-Ferrand (FR)

(72) Inventors: Rejane Dastillung, Lyons (FR); Sophie Couderc, Neuilly sur Seine (FR); Olivier Thinon, Roanne (FR)

(73) Assignees: IFP Energies nouvelles, Rueil-Malmaison (FR); Compagnie Generale des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 16/314,194

(22) PCT Filed: Jun. 26, 2017

(86) PCT No.: PCT/EP2017/065742
§ 371 (c)(1),
(2) Date: Dec. 28, 2018

(87) PCT Pub. No.: WO2018/001982
PCT Pub. Date: Jan. 4, 2018

(65) Prior Publication Data
US 2019/0202756 A1   Jul. 4, 2019

(30) Foreign Application Priority Data
Jun. 29, 2016   (FR) ...................................... 16 56049

(51) Int. Cl.
*C07C 1/20*   (2006.01)
*C07C 7/04*   (2006.01)
*C07C 7/08*   (2006.01)

(52) U.S. Cl.
CPC .................. *C07C 1/20* (2013.01); *C07C 7/04* (2013.01); *C07C 7/08* (2013.01)

(58) Field of Classification Search
None
See application file for complete search history.

(56) References Cited

U.S. PATENT DOCUMENTS

| | | | |
|---|---|---|---|
| 2016/0376206 A1* | 12/2016 | Dastillung | C07C 1/20 585/327 |
| 2017/0267604 A1* | 9/2017 | Dastillung | C07C 1/2072 |
| 2017/0291859 A1* | 10/2017 | Dastillung | C07C 45/002 |

FOREIGN PATENT DOCUMENTS

| | | |
|---|---|---|
| GB | 829021 A | 2/1960 |
| WO | 16042095 A1 | 3/2016 |

OTHER PUBLICATIONS

International Search Report PCT/EP2017/065742 dated Sep. 8, 2017pp. 1-4).

* cited by examiner

*Primary Examiner* — Ali Z Fadhel
(74) *Attorney, Agent, or Firm* — Millen, White, Zelano and Branigan, P.C.

(57) ABSTRACT

The invention relates to a process for producing butadiene from an ethanol feedstock comprising a step of converting ethanol into butadiene, a step of separating the reactants into a hydrated butadiene effluent, an impurities effluent and an ethanol-butadiene effluent, a separation step that separates the ethanol-butadiene effluent into a butadiene distillate and a contaminated reactants effluent, a step of purifying the butadiene by extractive distillation and an effluent treatment step.

15 Claims, 1 Drawing Sheet

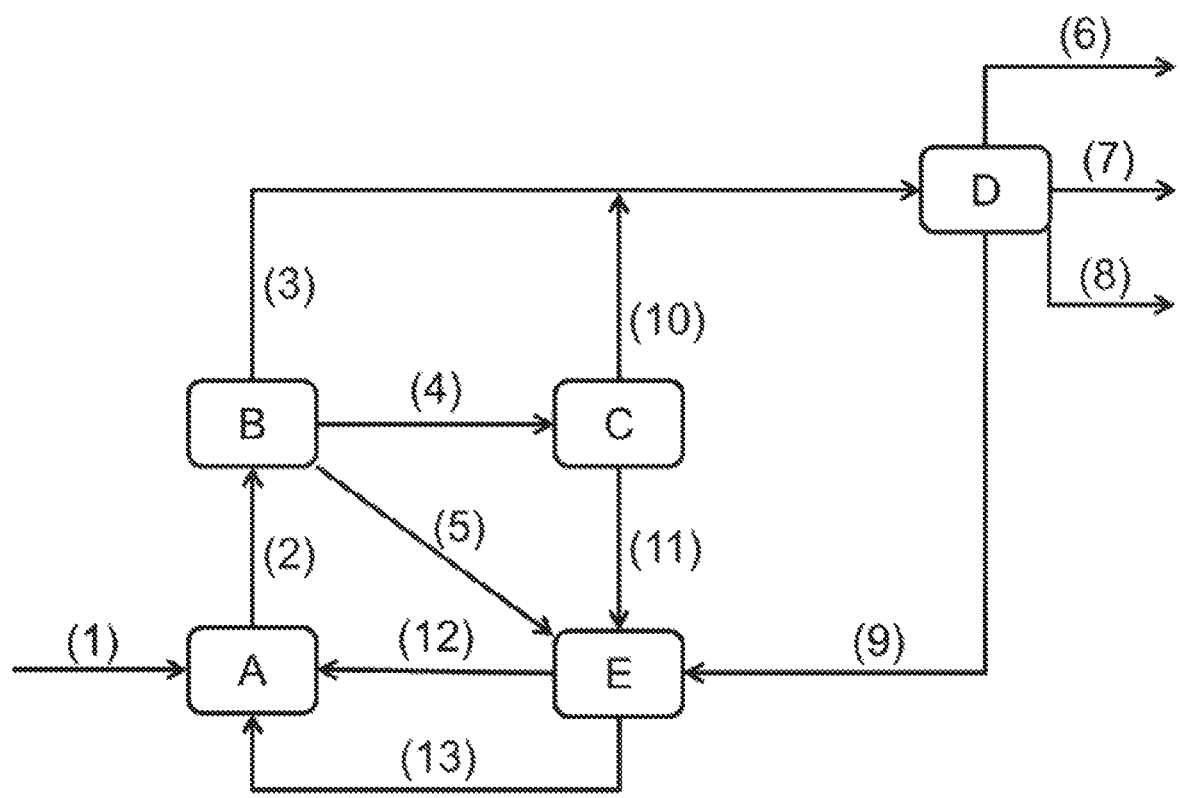

PROCESS FOR PRODUCING BUTADIENE FROM ETHANOL INTEGRATED WITH EXTRACTIVE DISTILLATION

TECHNICAL FIELD OF THE INVENTION

The invention relates to a process for producing butadiene from ethanol.

PRIOR ART

The process for producing 1,3-butadiene from ethanol, in one or two reaction steps, has a limited degree of conversion per pass. This leads to substantial recycling, made complex by the large number of impurities co-produced with the 1,3-butadiene, the extraction of which compromises the overall yield of the process. Each loss in the individual operations, in particular in the numerous separation operations, is thus reflected by an overall loss within the process, which rapidly becomes economically unacceptable. These losses led to the operation of these processes being suspended at the end of the Second World War.

Among the impurities, mention may be made of hydrocarbons comprising from 1 to 16 carbon atoms, which may be saturated or unsaturated, or even aromatic, and also oxygenated products such as alcohols, phenols, aldehydes, ketones, acids, esters, ethers and acetals, which may be saturated or unsaturated, or even aromatic.

Under normal temperature and pressure conditions, the main gaseous byproducts that may be mentioned include hydrogen, carbon monoxide, carbon dioxide, $C_1$-$C_4$ alkanes and olefins and methyl ethyl ether, and the main liquid byproducts that may be mentioned include pentenes, pentadienes, diethyl ether, ethyl vinyl ether, hexenes, hexadienes, butanal, crotonaldehyde, ethyl acetate, diethyl acetal, butanol, hexanol and acetic acid.

Other byproducts are generated in tiny amounts. In the rest of the document, the term "brown oils" will be used to denote as a whole hundreds of oxygenated and hydrocarbon compounds produced in reaction sections, the boiling points of which are between that of ethanol and ranging up to 600° C. A particular feature of these brown oils is that they are soluble in ethanol, but insoluble in water. They are liable, whenever they are not diluted with a large excess of ethanol, to foul and clog equipment. Moreover, these brown oils cause problems in the distillation column which separates the water produced by the reaction and the unconverted ethanol. Specifically, these brown oils are soluble in the water-ethanol effluent feeding said distillation column, and insoluble in the residue essentially constituted of water. A phase separation thus takes place within this column, considerably reducing the separation efficiency. Brown oils are difficult to remove during the process due to the fact that they are constituted of hundreds of compounds that have very different physicochemical properties. A fraction of these brown oils thus accumulates in the process, entailing a reduction in its efficiency after a few days and at best a few weeks of operation and necessitating periodic purging of certain streams. The loss of ethanol and acetaldehyde thereby occasioned degrades the overall yield of the process for a cost that would at the present time be prohibitive.

The purification of butadiene involves a combination of numerous individual operations, such as washes and simple and extractive distillations. The prior art teaches the use of extractive distillations using a solvent bis(2-chloroethyl) ether, or Chlorex, which is nowadays banned since it is highly toxic. It is important to note that the specifications for butadiene are nowadays extremely stringent, owing to the sensitivity of the butadiene polymerization catalysts. For example, the specification for acetaldehyde (intermediate reactant for producing butadiene) in butadiene has gone from 1000 ppm to less than 10 ppm at the present time. The publication "Synthetic rubber from Alcohol", (A. Talalay, M. Magat, 1945) gives a general view of the processes developed up to the 1940s.

U.S. Pat. No. 2,409,250 describes the successive steps for the purification of butadiene (extraction, first purification and final purification of butadiene by super-fractionation). Butadiene is produced in a purity of 98.7%, but at the expense of a significant loss of yield. To limit this loss, the overhead products from the column for butadiene purification by superfractionation are removed and partly recycled into the butadiene extraction step. This substantial recycling, in particular the recycling of the butene/butadiene stream in order to remove the noncondensable gas, entails oversizing of the equipment.

U.S. Pat. No. 1,948,777 describes in detail the final step of butadiene purification by extractive distillation using various solvents, including Chlorex. By limiting the loss of butadiene at the top of the column, i.e. a concentration of 0.2% of butadiene in the distillate, the purity of the butadiene obtained at the bottom is only 70%, whereas by seeking to obtain a purer butadiene at the bottom, i.e. 99%, the loss of butadiene at the top is much greater, with a butadiene concentration in the distillate of 30%. The production of a high-purity butadiene is thus achieved at the expense of a very great reduction in the overall yield of the unit.

WO 14199348 describes a method for obtaining butadiene from an effluent containing ethanol and optionally acetaldehyde over a catalyst based on a zeolite material. Ethanol conversions of greater than 95% and butadiene selectivities of between 20% and 48% are obtained. The patent mentions the production of oxygenated compounds such as diethyl ether, crotonaldehyde and ethyl acetate, which are separated from the butadiene by distillation, without giving any further details. No information is given regarding the management of the numerous other impurities that may be present or regarding the means for purifying the butadiene in order to meet the specifications required regarding its use in downstream processes.

The catalyst becomes deactivated in the course of its use, the consequence being a degradation in the butadiene selectivity and the production of a larger amount of impurities such as 1-butyne, 1,2-butadiene, n-butane and butenes. These impurities become partially or totally entrained with the butadiene in the steps for separating said butadiene from acetaldehyde and ethanol.

WO 2016/042096 and WO 2016/042095 describe a process for producing butadiene from an ethanol feedstock, in one and two reaction steps, respectively, with an arrangement of individual operations enabling the removal of the gaseous and liquid impurities while at the same time minimizing the loss of ethanol and acetaldehyde, thus improving the overall yield of the unit while reducing the overall flow of water required in the separation steps and obtaining a very pure butadiene. In these processes, the ethanol feedstock is used to wash the effluent from the reaction section in order to solubilize the butadiene present in the vapour effluent which would otherwise be partly purged with the light gases. The ethanol feedstock is therefore brought into contact with impurities before being fed to the reaction steps. The final purification of the butadiene is performed by liquid-liquid extraction. However, specific impurities such as butynes may be produced in critical contents with regard to the specification for the butadiene product obtained via the process when the catalysts become deactivated. This problem is not addressed in these patents. Moreover, the proposed liquid-liquid extraction step requires pre-purification of the butadiene effluent to remove the light compounds, the residual water and oxygenated compounds such as acetaldehyde, ethanol or diethyl ether.

At the present time, the main source of butadiene is oil. This butadiene is extracted from a $C_4$ fraction produced by steam cracking of naphtha, containing between 35% and 60% by weight of butenes/butanes, between 30% and 60% by weight of butadiene, typically 0.5% to 2% by weight (sometimes more) of acetylenes, in particular vinylacetylene, and also a small amount of 1,2-butadiene (about 0.1% by weight) and light compounds such as propane and propylene. The extraction is performed by extractive distillation with a polar aprotic solvent, in a purity of greater than 99.5% by weight and a yield generally greater than 98% by weight. Extractive distillations using N-methylpyrrolidone (NMP), dimethylformamide (DMF) and acetonitrile (ACN) as solvent are the ones most used and the most widespread.

Extractive distillation applied to the $C_4$ fractions derived from steam cracking is one alternative, but its extrapolation to the butadiene effluents derived from production processes starting with ethanol is not obvious on account of various compositions, namely a butadiene concentration of greater than 80% by weight and a concentration of butenes and butanes of less than 15% by weight, a globally lower content of acetylenes and the potential presence of oxygenated compounds such as acetaldehyde, diethyl ether (DEE) and water, and of alkynes produced with the gradual deactivation of the catalysts.

OBJECTIVE AND ADVANTAGE OF THE INVENTION

The invention relates to a process for producing butadiene from an ethanol feedstock comprising at least 80% by weight of ethanol, said process comprising:
A) a step of converting ethanol into butadiene comprising at least one reaction section fed with at least one fraction of said ethanol feedstock and with at least one fraction of the ethanol effluent resulting from step E), carried out at a pressure between 0.1 and 1.0 MPa and at a temperature between 200° C. and 500° C. in the presence of a catalyst, and producing at least one reaction effluent;
B) a step of separating the reactants which is fed at least with said reaction effluent and that produces at least an ethanol-butadiene effluent, an impurities effluent and a hydrated butadiene effluent;
C) a separation step fed at least with said ethanol-butadiene effluent and producing at least a butadiene distillate and a contaminated reactants residue;
D) a step of purifying the butadiene comprising:
   a section for separating the 1-butene comprising an extractive distillation, fed with said hydrated butadiene effluent resulting from step B), as a mixture with said butadiene distillate resulting from step C) and with a stream comprising a solvent, and separating, as overhead, a light gas effluent, and, as bottoms, a butadiene residue, and also comprising a distillation fed with said butadiene residue and separating, as overhead, a topped butadiene distillate and, as bottoms, a solvent residue;
   a section for separating the oxygenated compounds comprising an extractive distillation fed with said topped butadiene distillate resulting from the 1-butene separation section and by a stream comprising a solvent and producing, as overhead, a prepurified butadiene effluent, and, as bottoms, a spent solvent residue and also comprising a distillation fed with said spent solvent residue and separating, as overhead, an oxygenated compounds effluent and, as bottoms, a solvent residue;
   a final distillation section fed with said prepurified butadiene effluent resulting from the section for separating the oxygenated compounds separating, as overhead, a purified butadiene effluent and, as bottoms, a 2-butene residue;
E) an effluent treatment step fed at least with the contaminated reactants residue resulting from step C) and with the oxygenated compounds effluent resulting from step D), and producing at least an ethanol effluent, an ethanol-acetaldehyde effluent, and one or more brown oil effluents.

The process according to the invention enables a significant energy saving with respect to the prior art. In particular, the absence of treatment of the vapour fraction of the reaction effluent by washing with a stream of ethanol followed by washing with water makes it possible to reduce the flow rates of ethanol and water in the effluent treatment sections and, owing to this reduction, to calm said sections.

The process according to the invention also makes it possible to produce a butadiene to the specifications, even when byproducts, in particular butynes, are generated in a larger amount due to the deactivation of the catalysts used in the reaction steps, with no loss of overall yield and with a maintained energy saving.

DETAILED DESCRIPTION OF THE INVENTION

Feedstock

The ethanol feedstock used in the process according to the invention may originate from any fossil, plant or animal origin, and in particular from processes for producing ethanol from plant resources. Said feedstock comprises at least 80% by weight of ethanol, preferentially at least 90% by weight, and preferably at least 93% by weight. Very preferably, said ethanol feedstock corresponds to the EN 15376 fuel ethanol specifications.

Step A) of Converting Ethanol into Butadiene

The process according to the invention comprises a step A) of converting ethanol into butadiene.

Said step A) comprises at least one reaction section fed with at least one fraction of said ethanol feedstock and with at least one fraction of the ethanol effluent resulting from step E), carried out at a pressure between 0.1 and 1.0 MPa and at a temperature between 200° C. and 500° C. in the presence of a catalyst, and producing at least one reaction effluent.

In a first particular arrangement of the process according to the invention, said reaction section of said step A) comprises a reaction zone, fed with at least one fraction of said ethanol feedstock and with at least one fraction of the ethanol effluent resulting from step E), making it possible to convert the ethanol into at least butadiene. It is operated in the presence of any catalyst known to those skilled in the art, for example a silica/magnesium oxide catalyst, at a temperature advantageously between 300° C. and 400° C., preferably between 320° C. and 370° C. and at a pressure advantageously between 0.1 and 0.5 MPa, preferably between 0.1 and 0.3 MPa.

In a second particular arrangement of the process according to the invention, said reaction section of said step A) comprises two reaction zones, the first one, fed with at least one fraction of said ethanol feedstock and with at least one fraction of the ethanol effluent resulting from step E), making it possible to convert the ethanol into acetaldehyde, and the second one, fed with the effluent from the first reaction zone, with the residual fraction of said ethanol effluent resulting from step E) and with at least one fraction of the ethanol-acetaldehyde effluent resulting from step E), making it possible to convert the mixture of ethanol and acetaldehyde into at least butadiene. The effluent from the second reaction zone constitutes the reaction effluent of said step A).

Advantageously, in this second arrangement, a gas-liquid separation means is used between the two reaction zones in order to separate the effluent from the first reaction section into a gas effluent and a liquid effluent. The gas effluent, comprising in particular hydrogen, may be treated in the same way as the hydrogen effluent according to the hydrogen treatment steps C1) and C2) described in WO 2016/042095. The liquid effluent feeds the second reaction section.

In this second arrangement, said first reaction zone is operated in the presence of a catalyst comprising a copper oxide, or any other suitable catalyst well known to a person skilled in the art.

The ethanol/acetaldehyde molar ratio at the inlet of said second reaction zone is between 1 and 5, preferably between 1 and 3.5, more preferably still between 2 and 3.5 and very preferably between 2.2 and 3.5. Said second reaction zone is operated in the presence of a catalyst, advantageously a silica-supported catalyst selected from the group consisting of catalysts comprising tantalum oxide, zirconium oxide or niobium oxide, preferentially comprising 2% tantalum oxide (see for example Corson, Jones, Welling, Hincbley, Stahly, Ind. Eng Chem. 1950, 42, 2, 359-373). Said second reaction zone is operated at a temperature of between 300° C. and 400° C., preferably between 320° C. and 370° C. and at a pressure of between 0.1 and 1.0 MPa, preferably between 0.1 and 0.5 MPa, preferably between 0.1 and 0.3 MPa.

The reaction effluent from said reaction zone in the first particular arrangement according to the invention, or from said second reaction zone in the second particular arrangement according to the invention, still comprises ethanol, and also numerous impurities produced with the butadiene, among which are hydrogen, ethylene, propylene, diethyl ether (DEE), ethyl acetate, butanol, hexanol, butenes, butynes, pentenes, pentadienes, hexenes, hexadienes, crotonaldehyde, butyraldehyde, diethyl acetal and acetic acid. It feeds the reactant separation step B).

Reactant Separation Step B)

The process according to the invention comprises a step B) of separating the reactants which is fed at least by said reaction effluent and that produces at least an ethanol-butadiene effluent, an impurities effluent and a hydrated butadiene effluent.

Said step B) makes it possible to separate, on the one hand, an ethanol-butadiene liquid effluent predominately comprising, i.e. at more than 50% by weight, the ethanol and acetaldehyde reactants that have not reacted, and also comprising butadiene and, on the other hand, a hydrated butadiene vapour effluent predominately comprising, i.e. at more than 50% by weight, butadiene.

In a first preferred arrangement, said step B) comprises:
a gas-liquid separation section that separates said reaction effluent into a liquid effluent constituting said ethanol-butadiene effluent and a gas effluent,
a compression section that compresses said gas effluent to give a compressed gas effluent,
a distillation section fed with said compressed gas effluent and that separates, as overhead, said hydrated butadiene effluent and, as bottoms, said impurities effluent.

Said gas-liquid separation section of said first arrangement uses gas-liquid separation means known to a person skilled in the art. Said means are operated at a pressure of between 0.1 and 0.3 MPa and at a temperature of between 10° C. and 50° C.

In a first preferred variant of said first arrangement, said gas-liquid separation section is operated at a temperature of between 10° C. and 20° C., preferentially between 12° C. and 17° C. This operating temperature makes it possible to separate in the gas effluent between 85% and 90% of the butadiene included in the reaction effluent, said gas effluent then containing more than 80% of butadiene. The flow rate feeding the compressor is reduced relative to the second variant presented below. The content of ethanol, acetaldehyde, water and impurities in said gas effluent is also reduced relative to the second variant presented below.

In a second preferred variant of said first arrangement, said separation section is operated at a temperature of between 40° C. and 50° C., preferentially between 42° C. and 47° C. This operating temperature makes it possible to separate in said gas effluent between 90% and 96% of the butadiene included in the reaction effluent, said gas effluent then containing more than 60% of butadiene. The flow rate to step C is thus reduced relative to the first variant and the loss of butadiene is limited.

Said compression section of said first arrangement compresses said gas effluent to a pressure of between 0.1 and 1.0 MPa, preferentially between 0.1 and 0.7 MPa and preferably between 0.2 and 0.5 MPa. The objective of this section is mainly to reduce the volume flow rate of gas to be treated.

Said distillation section of said first arrangement separates, as overhead, said hydrated butadiene effluent which comprises more than 90% by weight, advantageously more than 95% by weight, and preferably more than 98% by weight, preferentially more than 99% by weight of the butadiene included in said compressed gas effluent and, as bottoms, said impurities effluent. Said impurities effluent is advantageously sent to the effluent treatment step E) as a mixture with the contaminated reactants residue resulting from step C).

In a second preferred arrangement, said step B) comprises:
a first gas-liquid separation section that separates said reaction effluent into a liquid effluent constituting said impurities effluent and a gas effluent, operated at a temperature of between 70° C. and 80° C., and a pressure of between 0.1 and 0.3 MPa,
a compression section that compresses said gas effluent to give a compressed gas effluent,
a second gas-liquid separation section fed with said compressed gas effluent and that separates, as gas phase, said hydrated butadiene effluent and, as liquid phase, said ethanol-butadiene effluent, operated at a temperature of between 40° C. and 50° C. and a pressure of between 0.2 and 0.6 MPa.

Said first gas-liquid separation section of said second arrangement uses gas-liquid separation means known to a person skilled in the art. Said means are operated at a pressure of between 0.1 and 0.3 MPa and at a temperature of between 70° C. and 80° C. The operation of said section at high temperature has the effect of minimizing the content of butadiene (to less than 0.1% by weight) in said impurities effluent that then directly feeds step E) without it being necessary to pass through step C) in order to recover the butadiene.

Said compression section of said second arrangement compresses said gas effluent to a pressure of between 0.1 and 1.0 MPa, preferentially between 0.1 and 0.7 MPa and preferably between 0.2 and 0.6 MPa. The objective of this section is mainly to reduce the volume flow rate of gas to be treated.

Said second gas-liquid separation section of said second arrangement uses gas-liquid separation means known to those skilled in the art. Said means are operated at a pressure of between 0.2 and 0.6 MPa and at a temperature of between 40° C. and 50° C. The operation of said second section at a lower temperature has the effect of reducing the amount of ethanol, acetaldehyde, diethyl ether and other oxygenated compounds present in said hydrated butadiene effluent sent to step D).

In a preferred variant of said second arrangement, said hydrated butadiene effluent resulting from said second gas-liquid separation section feeds a distillation section that aims to further reduce the amount of ethanol, acetaldehyde and diethyl ether present in said hydrated butadiene effluent. This distillation section separates from said hydrated butadiene effluent, as bottoms, an oxygenated compounds residue and, as overhead, a hydrated butadiene effluent depleted in oxygenated compounds, said effluent comprising more than 90% by weight, advantageously more than 95% by weight, and preferably more than 98% by weight, preferentially more than 99% by weight of the butadiene included in said hydrated butadiene effluent feeding said distillation section. Said hydrated butadiene effluent depleted in oxygenated compounds then feeds step D) as hydrated butadiene effluent. Said oxygenated compounds residue advantageously feeds said effluent treatment step E) as a mixture with said contaminated reactants residue resulting from step C).

In another preferred variant of said first or of said second arrangement, said hydrated butadiene effluent obtained at the end of said distillation section, or of said second gas-liquid separation section, feeds a water-washing section that aims to further reduce the amount of water-soluble polar compounds such as ethanol and acetaldehyde present in said hydrated butadiene effluent. This water-washing section comprises at least one gas-liquid washing section fed at the bottom with said hydrated butadiene effluent and at the top with a stream of water, advantageously originating from outside said butadiene production process, said washing section producing, as overhead, a hydrated butadiene effluent, depleted in oxygenated compounds, that feeds step D) and, as bottoms, a spent water raffinate. Said spent water raffinate contains soluble polar compounds such as acetaldehyde and a small amount of butadiene, and feeds the effluent treatment step E).

Separation Step C)

The process according to the invention comprises a separation step C) fed at least by said ethanol-butadiene effluent resulting from step B) and producing at least a butadiene distillate and a contaminated reactants residue.

The ethanol-butadiene effluent resulting from step B) feeds said separation step C) so as to separate, as overhead, a butadiene distillate comprising most of the butadiene and, as bottoms, a contaminated reactants residue. The term "most" means more than 80% by weight of the butadiene included in the feed of said feed of said step C), preferentially more than 90%, preferably more than 95%, even more preferably more than 98%, very preferably more than 99% and very advantageously more than 99.5% by weight of the butadiene included in said feed of said step C).

This contaminated reactants residue comprises ethanol and acetaldehyde, and also comprises water and byproducts formed in step A), for instance diethyl ether, ethyl acetate and brown oils. Said contaminated reactants residue then feeds the effluent treatment step E). Said separation step C) is operated at a pressure of between 0.1 and 1 MPa and preferably between 0.2 and 0.5 MPa. This step is advantageously carried out by distillation.

The arrangement of the steps of the process according to the invention, in particular the implementation of separation by extractive distillations in step D) makes it possible to be less strict regarding the amount of oxygenated compounds in the butadiene distillate. Specifically, ethanol, acetaldehyde and diethyl ether may together represent up to 60% by weight thereof.

Butadiene Purification Step D)

The process according to the invention comprises a butadiene purification step D) comprising:

a section for separating the 1-butene fed at least by the hydrated butadiene effluent resulting from step B), as a mixture with said butadiene distillate resulting from step C) and producing a light gas effluent and a topped butadiene distillate;

a section for separating the oxygenated compounds fed at least by said topped butadiene distillate resulting from the 1-butene separation section and producing a prepurified butadiene effluent and an oxygenated compounds effluent;

a final distillation section fed with said prepurified butadiene effluent resulting from the section for separating the oxygenated compounds separating, as overhead, a purified butadiene effluent and, as bottoms, a 2-butene residue.

Said step D) is fed with the hydrated butadiene effluent resulting from step B) as a mixture with the butadiene distillate resulting from step C). Said mixture comprises at least 50% by weight, preferably at least 60% by weight, preferably at least 70% by weight, very preferably at least 80% by weight of butadiene and also impurities, due in particular to the degradation of the selectivity towards butadiene in the reaction section, among which are oxygenated compounds that are not desired in the purified butadiene effluent such as ethanol, acetaldehyde, diethyl ether and water, and at most 15% by weight of $C_4$ impurities such as butenes and butanes, hydrocarbons comprising at least 5 carbon atoms ($C_5^+$ hydrocarbons) and also light gases, in particular hydrogen, ethane, ethylene, propane and propylene.

Said 1-butene separation section comprises an extractive distillation fed with said hydrated butadiene effluent, as a mixture with said butadiene distillate and with a stream comprising a solvent, and separating, as overhead, a light gas effluent and, as bottoms, a butadiene residue.

The term "solvent" means any polar solvent that is miscible in liquid phase with said butadiene feedstock under the operating conditions of said extractive distillation, having a volatility lower than that of the compounds 1,3-butadiene, 2-butene and butynes, so as to remain in the liquid phase in said 1-butene separation section, but being able to be separated from these compounds by distillation. Said solvent is advantageously selected from the group consisting of dimethylformamide (DMF), N-methylpyrrolidone and acetonitrile.

The hydrated butadiene effluent, as a mixture with said butadiene distillate, is advantageously compressed in a compression section to a pressure of between 0.1 and 1.0 MPa, preferentially between 0.1 and 0.7 MPa, and preferably between 0.2 and 0.5 MPa. The effect of this compression is to reduce the volume flow rate of gas.

In the preferred case in which said solvent is DMF, since the water-DMF mixture is corrosive, the water content in the hydrated butadiene effluent, as a mixture with said, advantageously compressed, butadiene distillate, should be adjusted in accordance with the metallurgical constraints. Furthermore, the corroded elements will have a tendency to catalyze the butadiene polymerization reaction, leading to a loss of yield and a risk of clogging of the lines. The water content may be reduced via any means known to those skilled in the art, for example by drying, advantageously by drying over an adsorbent, the adsorbent possibly being silica-based and/or alumina-based. In a non-limiting manner, this adsorbent may be a zeolite such as a zeolite 3A or 4A. Advantageously, the water content in the hydrated butadiene effluent, as a mixture with said, advantageously compressed, butadiene distillate, is reduced to a value of less than 3% by weight of said effluent. It is also possible to add a corrosion inhibitor known to those skilled in the art to said effluent.

The light gas effluent produced at the top of the extractive distillation of said 1-butene separation section comprises 1- and 2-butenes and also light gases such as hydrogen, ethane, ethylene, propane and propylene. When the content of light gases in the hydrated butadiene effluent, as a mixture with said butadiene distillate, is high, for example greater than 2% of the total weight of said effluent, substantial cooling of the top of said extractive distillation may be necessary in order to ensure a sufficient reflux in said column. This cooling is conventionally performed using a refrigeration unit.

The light gas effluent may be burnt to provide some of the heat required for the hot oil circuit or the steam boilers of the process. The arrangement of the steps of the process according to the invention make it possible to produce a light gas effluent at a pressure level sufficient to be sent to a furnace or to a system for elimination by combustion (flare).

Advantageously, said hydrated butadiene effluent, as a mixture with said butadiene distillate, is prewashed by placing in contact with a stream comprising a polar solvent selected from the group consisting of dimethylformamide (DMF), N-methylpyrrolidone (NMP) and acetonitrile, prior to being fed into said 1-butene separation section. This prewashing makes it possible to separate most of the light gases and thus to dispense with cooling requiring the use of a refrigeration unit at the top of said extractive distillation.

Said extractive distillation is operated so that said butadiene residue comprises at least 95% by weight, advantageously at least 98% by weight and preferably at least 99% by weight of the butadiene included in said hydrated butadiene effluent, as a mixture with said butadiene distillate. Said extractive distillation is also operated such that the amount of 1-butene in said butadiene residue represents at most 0.5% of the weight of butadiene included in said residue. The operation is performed by adjusting the ratio of the flow rate of solvent to the flow rate of butadiene effluent, and also the degree of reflux of the extractive distillation, as is known to those skilled in the art.

Said extractive distillation is operated at the lowest possible pressure to limit the exposure of the butadiene-rich streams to high temperatures at which polymerization or decomposition might take place. Preferably, the operating pressure of said section is less than 0.6 MPa and preferably less than 0.5 MPa.

Said 1-butene separation section also comprises a distillation fed with said butadiene residue and separating, as overhead, a topped butadiene distillate and, as bottoms, a solvent residue.

The distillation is a conventional distillation known to those skilled in the art, performed such that said solvent residue comprises less than 1% by weight of butadiene, and advantageously no longer comprises any butadiene, and such that said topped butadiene distillate comprises less than 0.5% by weight of solvent, and advantageously no longer comprises any solvent.

Said distillation is advantageously operated at the lowest possible pressure to limit the exposure of the butadiene-rich streams to high temperatures at which polymerization or decomposition might take place. Said distillation is advantageously operated at a head temperature of less than 60° C., preferably less than 50° C., and at a head pressure of less than 0.5 MPa, preferably less than 0.4 MPa.

Said solvent residue advantageously feeds the 1-butene separation section as a stream comprising a solvent, advantageously as a mixture with make-up solvent.

Said section for separating the oxygenated compounds comprises an extractive distillation fed with said topped butadiene distillate and with a stream comprising a solvent and produces, as overhead, a prepurified butadiene effluent and, as bottoms, a spent solvent residue.

Said solvent is advantageously chosen from the group constituted by dimethylformamide (DMF), N-methylpyrrolidone (NMP) and acetonitrile.

Said extractive distillation is operated such that said prepurified butadiene effluent comprises at least 98% by weight, advantageously at least 99% by weight of the butadiene included in said topped butadiene distillate. Said extractive distillation is also operated such that the content of alkynes containing 4 carbon atoms present in the purified butadiene effluent at the top of the final distillation section complies with the specifications required for the subsequent use of said effluent. The operation is performed by adjusting the ratio of the flow rate of solvent to the flow rate of topped butadiene distillate, and also the degree of reflux of said extractive distillation, as is known to those skilled in the art.

Said extractive distillation is operated at the lowest possible pressure to limit the exposure of the butadiene-rich streams to high temperatures at which polymerization or decomposition might take place. Preferably, the operating pressure of said distillation is less than 0.6 MPa and preferably less than 0.5 MPa.

Said section for separating the oxygenated compounds also comprises a distillation fed with said spent solvent residue and separating, as overhead, an oxygenated compounds effluent and, as bottoms, a solvent residue.

The distillation is a conventional distillation known to those skilled in the art, operated such that said solvent residue comprises less than 1% by weight of butadiene, and advantageously no longer comprises any butadiene, and such that the loss of solvent in said oxygenated compounds effluent is less than 0.05% by weight, preferably less than 0.01% by weight. The term "loss of solvent" means the ratio of the flow rate of solvent in said oxygenated compounds effluent to the flow rate of solvent in said spent solvent residue. Said oxygenated compounds effluent therefore comprises, besides the oxygenated compounds, alkynes containing 4 carbon atoms.

Said distillation is also operated such that the content of acetylenic compounds in said oxygenated compounds effluent does not exceed 30% by weight to avoid any risk of explosion promoted by an increase in the pressure and the temperature, this phenomenon being known to those skilled in the art.

Said distillation is advantageously operated at a head temperature of less than 60° C., preferably less than 50° C., and at a head pressure of less than 0.5 MPa, preferably less than 0.4 MPa.

Said solvent residue advantageously feeds the section for separating the oxygenated compounds as a stream comprising a solvent, advantageously as a mixture with make-up solvent.

The solvent residue resulting from the 1-butene separation section and the solvent residue resulting from the section for separating the oxygenated compounds may advantageously be mixed before feeding the 1-butene separation section and the section for separating the oxygenated compounds as a stream comprising a solvent. All or some of the solvent residue resulting from the 1-butene separation section and optionally from the section for separating the oxygenated compounds may advantageously be sent to a section for purification of the solvent, for example by distillation or any other operation known to those skilled in the art, to separate out the heavy impurities.

Said step D) comprises a final distillation section fed with said prepurified butadiene effluent, separating, as overhead, a purified butadiene effluent and, as bottoms, a 2-butene residue.

This section makes it possible to remove the heavy impurities, and especially the traces of cis-2-butenes, and also the residual 1-butynes and the 1,2-butadiene that may be present in the topped butadiene distillate.

Said purified butadiene effluent comprises at least 99.5% by weight of butadiene. The yield for the purification step D) according to the invention, defined as the flow rate of butadiene in the purified butadiene effluent over the flow rate of butadiene in the hydrated butadiene effluent, as a mixture with said butadiene distillate feeding step D), is at least equal to 95% by weight, preferably to 98%, preferably greater than 99% by weight.

Effluent Treatment Step E)

The process according to the invention comprises an effluent treatment step E) fed at least by the contaminated reactants residue resulting from step C) and by the oxygenated compounds effluent resulting from step D), and producing at least an ethanol effluent, an ethanol-acetaldehyde effluent, a light brown oil effluent and a heavy brown oil effluent.

Preferably, said step E) comprises at least a washing/backwashing section, a section for distilling the light brown oils, a section for distilling the heavy brown oils, an acetaldehyde separation section and an ethanol-water separation section.

Said preferential washing/backwashing section is fed at an intermediate point by said contaminated reactants residue resulting from step C), as a mixture with said oxygenated compounds effluent resulting from step D), advantageously as a mixture with the impurities effluent resulting from step B), advantageously as a mixture with the oxygenated compounds residue resulting from step B).

Said preferential washing/backwashing section is fed at the bottom by a hydrocarbon effluent and at the top by at least one fraction of the recycled water residue resulting from the ethanol-water separation section. Said washing/backwashing section may also be fed with a stream of water external to the process in addition to and/or as a replacement for said fraction of the recycled water residue. The hydrocarbon effluent and the fraction of the recycled water residue are fed at a temperature preferably between 10° C. and 70° C., preferentially between 45° C. and 55° C. Said washing/backwashing section produces, as overhead, a washing hydrocarbon extract loaded with a fraction of the impurities and of the brown oils, and, as bottoms, an ethanol/acetaldehyde/water raffinate.

Said washing/backwashing section is preferably operated at a pressure of between 0.1 and 0.5 MPa, preferentially between 0.2 and 0.4 MPa. Preferably, the addition of water to perform the backwashing is such that the water content in the water/ethanol/acetaldehyde raffinate is greater than 30% by weight, preferably greater than 40% by weight.

In one embodiment, the contact between the two liquid phases in said washing/backwashing section takes place in a liquid-liquid extractor. Various contact methods may be envisaged. Mention may be made, in a non-limiting manner, of a packed column, a pulsed column, or an agitated partitioned column. In another embodiment, the contact between the two liquid phases in said washing/backwashing section takes place in a membrane contactor, or a cascade of membrane contactors. This contact method is particularly well suited to the system used. Specifically, water-ethanol-hydrocarbon mixtures are known to form stable emulsions, which may be problematic in a liquid-liquid extractor. The membrane contactor makes it possible to generate a substantial area of contact, promoting the transfer of the impurities and oils to the hydrocarbon phase, without generating an emulsion.

Said washing hydrocarbon extract feeds said light brown oil distillation section, which produces as distillate said light brown oil effluent, and a hydrocarbon residue comprising the heavy fraction of the brown oils.

Said light brown oil effluent is composed of impurities produced in the reaction section of step A), mainly diethyl ether, ethyl acetate and crotonaldehyde, and also of the light fraction of the brown oils, composed of impurities in a smaller amount, among which are pentene, isoprene, butanal and vinyl ethyl ether. This effluent may be burnt to provide some of the heat required for the hot oil circuit or for the steam boilers of the process, or distilled to recover a diethyl ether effluent and/or an ethyl acetate/crotonaldehyde effluent, which may either be upgraded, or recycled into the reaction section of step A) to be retransformed.

Said hydrocarbon residue essentially contains the hydrocarbons serving for washing, but also the heaviest fraction of the brown oils. To avoid accumulation of the brown oils by recycling of the hydrocarbon effluent into the liquid-liquid extractor, a fraction of said hydrocarbon residue is treated in said heavy oil distillation section, consisting of a distillation column, which produces a hydrocarbon distillate essentially composed of hydrocarbons with a few remaining traces of brown oils and, as residue, said heavy brown oil effluent comprising more than 80%, preferentially more than 85% of hydrocarbons and also the heaviest brown oils. The fraction of said hydrocarbon effluent sent to said oil distillation section is between 5% and 30% of the total flow of said hydrocarbon residue, and preferentially between 10% and 20%. The hydrocarbon distillate is mixed with the fraction of the hydrocarbon residue that has not been treated in said heavy oil distillation section so as to form the hydrocarbon effluent feeding said washing/backwashing section.

This effluent, which preferably represents between 0.1% and 20% of the feedstock of said heavy oil distillation section, preferentially between 0.3% and 5%, may be burnt to provide some of the heat required for the hot oil circuit or the steam boilers of the process. Make-up hydrocarbons equivalent to the losses at the bottom of said heavy oil distillation section are necessary to keep the washing flow rate constant. This column is adjusted so as to keep constant the concentration of brown oils in the hydrocarbon recycling loop (hydrocarbon effluent/washing hydrocarbon effluent loop).

The light and heavy brown oil effluents are removed from the process.

The contaminated reactants residue resulting from step C) mainly comprises ethanol, acetaldehyde and water, but also impurities such as diethyl ether, ethyl acetate and the brown oils as defined previously. These impurities may accumulate if they are sent back to step A) in the ethanol-acetaldehyde effluent and/or the ethanol effluent and if they are only partially converted in the reaction section of step A). The washing/backwashing section makes it possible to recover some of these impurities before the acetaldehyde separation section and the water-ethanol separation section, which makes it possible to avoid the demixing of the brown oils in these sections.

The washing of the contaminated reactants residue resulting from step C) with a hydrocarbon effluent entrains certain impurities, whereas the backwashing of the hydrocarbon stream with a fraction of the recycled water residue (or where appropriate with a stream of water external to the process in addition to and/or as a replacement for said fraction of the recycled water residue) limits any loss of acetaldehyde and of ethanol.

Said hydrocarbon effluent may contain saturated and/or unsaturated and/or aromatic hydrocarbons, preferably saturated hydrocarbons. Said hydrocarbon effluent is advantageously constituted of a mixture of hydrocarbons containing between 6 and 40 carbon atoms, preferably between 10 and 20 carbon atoms. In a non-limiting manner, said hydrocarbon effluent may be a desulfurized gas oil or kerosene fraction or alternatively a hydrocarbon fraction produced by a unit of Fischer-Tropsch type.

The addition of water to the washing/backwashing section allows better functioning of the process for removing the impurities and brown oils according to the invention.

The process according to the invention thus avoids the regular purging of ethanol in order to avoid the accumulation of brown oils, which makes it possible to improve the overall performance of the process.

Said water/ethanol/acetaldehyde effluent obtained from the washing/backwashing section feeds said acetaldehyde separation section, in which the acetaldehyde is separated so as to form an ethanol-acetaldehyde effluent and an ethanol-water effluent. Said separation section advantageously carries out a distillation.

The ethanol-acetaldehyde effluent resulting from step E) is predominantly constituted of acetaldehyde and ethanol. The term "predominantly" means that the ethanol+acetaldehyde combination represents more than 80% by weight, preferably more than 85% by weight of said effluent. In a non-limiting manner, the ethanol-acetaldehyde effluent resulting from step E) may contain impurities such as water, ethyl acetate or acetone. The impurities other than water represent less than 10% and preferentially less than 8% by weight of the stream.

In one embodiment of the invention, said ethanol-acetaldehyde effluent undergoes a purification step before being recycled into the rest of the process. The term "purification" means placing said effluent in contact with adsorbents, for instance activated carbon, silica, alumina or else a functionalized polymeric resin.

Said ethanol-water effluent resulting from said acetaldehyde separation section feeds the ethanol-water separation section in which it is separated into an ethanol effluent and a recycled water residue.

Said ethanol-water separation section advantageously operates by distillation. At least a fraction of the ethanol feedstock from the process according to the invention may advantageously be introduced at the top of said distillation, the effect of which is to facilitate the distillation of the ethanol in the presence of impurities, to reduce the reflux and to increase the ethanol concentration in the ethanol effluent feeding the reaction section and thus to lower the total flow rate of this effluent for the same flow rate of ethanol, which makes it possible to work with a reaction section of smaller volume than in the prior art, in which the ethanol feedstock is first used for dissolving the butadiene in the vapour effluent of the reaction section.

This use of the ethanol feedstock according to the prior art has the advantage of making it possible to extract the lightest compounds included in the effluent from the reaction section, these compounds being separated by successive washes with the ethanol feedstock and with a stream of water. In the process according to the invention, these light compounds remain with the butadiene up to the butadiene purification step, the consequence of which is to increase the size of the equipment and may, depending on the concentration of light compounds, impose the use of a pre-washing step or of refrigeration units at the top of the 1-butene separation sections so as to ensure the liquefaction of part of the distillate and to ensure reflux. This choice is thus, in principle, detrimental to the performance of the process. Now, the Applicant has realized that feeding of the ethanol feedstock at the top of a water-ethanol separation section in combination with a butadiene purification step performed by extractive distillation and which is more capable of managing the light compounds, despite the sending of the light compounds to the separation step C) (which in principle has a negative impact since it is more energy-consuming), resulted overall in an improvement in the performance of the process according to the invention, in particular by improving the functioning of the water-ethanol separation section and by minimizing the ethanol-acetaldehyde reaction in the washing/backwashing section.

In one embodiment of the invention, the ethanol effluent undergoes a purification step before feeding the conversion step A). The term "purification" means placing said effluent in contact with adsorbents, for instance activated carbon, silica, alumina or else a functionalized polymeric resin. For example, an activated carbon makes it possible to remove the traces of butanol and hexanol.

The ethanol effluent predominantly comprises ethanol. The term "predominantly" means that the ethanol represents more than 80% by weight, preferably more than 84% by weight of said effluent. In a non-limiting manner, the ethanol-rich effluent may contain impurities such as water, ethyl acetate, butanol and hexanol. The impurities other than water represent less than 10%, in a favoured manner less than 5% and more preferentially less than 2% by weight of said effluent.

BRIEF DESCRIPTION OF THE DRAWINGS

FIG. 1 schematically shows a general view of an arrangement of the process according to the invention.

A step A of converting ethanol into butadiene is fed with an ethanol feedstock (1), and with the ethanol effluent (13) and with the ethanol-acetaldehyde effluent (12) resulting from step E. This step produces a reaction effluent (2) which feeds a reactant separation step B, which produces an ethanol-butadiene effluent (4), an impurities effluent (5) and a hydrated butadiene effluent (3). In the arrangement shown in FIG. 1, the impurities effluent (5) feeds the effluent treatment step E.

The ethanol-butadiene effluent (4) feeds the separation step C so as to produce a butadiene distillate (10) and a contaminated reactants residue (11).

The butadiene distillate (10), as a mixture with the hydrated butadiene effluent (3) feed the butadiene purification step D. Step D produces a light gas effluent (6), an oxygenated compounds effluent (9), a 2-butene residue (8) and, as product of the process, a purified butadiene effluent (7).

The oxygenated compounds effluent (9) and the contaminated reactants residue (11) feed the effluent treatment step E so as to produce an ethanol effluent (13), an ethanol-acetaldehyde effluent (12), a light brown oils effluent and a heavy brown oils effluent (not represented).

EXAMPLES

The examples that follow are based on simulations integrating the recycling of the streams. In each of the examples, the flow rate of ethanol feedstock is adjusted so as to obtain an annual production of 150 kt/year of a purified butadiene effluent in a purity of between 99.5% and 100% by weight.

All the percentages are weight percentages.

Example 1—Comparative

A process for producing butadiene from ethanol in accordance with the process described in WO 2016/042095 is fed with 48.2 t/h of an ethanol feedstock comprising 93.4% by weight of ethanol. This scheme does not involve extractive distillation and the ethanol feedstock is used to wash the reaction effluent.

The ethanol feedstock is used to wash the vapour effluent obtained from the reaction section, after said vapour effluent was separated from its liquid part and compressed.

The ethanol feedstock obtained from the washing section is mixed with the liquid part of the effluent from the reaction section, forming a stream of 166 t/h comprising 54% ethanol, 4% acetaldehyde, 23% water and 11% butadiene.

This stream is treated in a distillation section producing, as overhead, 20 t/h of a distillate comprising butadiene and 146 t/h of a residue no longer comprising any butadiene, and comprising 61% ethanol, 4% acetaldehyde and 27% water.

The distillate comprising the butadiene is successively treated by washing with water, drying, cryogenic distillation and separation with DMSO so as to produce 18.75 t/h of a purified butadiene effluent comprising 99.6% butadiene. The washing with water uses 21 t/h of water originating from outside the process. The water obtained from the washing of the distillate comprising the butadiene feeds the acetaldehyde separation section.

The vapour effluent washed with the ethanol feedstock is washed with water obtained from the effluent treatment so as to take up the traces of ethanol and acetaldehyde. The water obtained from this washing (about 0.4 t/h) feeds a water-ethanol separation section.

The 146 t/h of residue are treated in a washing/backwashing section with hydrocarbons so as to separate out the impurities, and in particular the brown oils. The effluent from this section, representing 168 t/h and comprising 53% ethanol, 4% acetaldehyde and 40% water, feeds two distillation columns making it possible to separate an ethanol-acetaldehyde effluent, an ethanol effluent and a water effluent, which is partly (29.5 t/h) recycled into the washing of the vapour effluent obtained from the reaction section (0.4 t/h) and into the washing/backwashing section (29.1 t/h), and partly (41.4 t/h) purged.

The ethanol effluent (95.7 t/h comprising 79% ethanol) and the ethanol-acetaldehyde effluent (23.2 t/h comprising 57% ethanol and 27% acetaldehyde) feed the reaction section.

The energy consumption of this scheme in terms of utilities (electricity, gas and steam) expressed in MWh is 178.8 MWh.

Example 2—in Accordance with the Invention

A process for producing butadiene from ethanol in accordance with the process according to the invention is fed with 48.2 t/h of an ethanol feedstock comprising 93.4% by weight of ethanol.

In accordance with the invention, the ethanol feedstock is not used to wash the vapour effluent obtained from the reaction section. The ethanol feedstock is fed into the top of the ethanol-water separation section, which separation is performed in a distillation column. This separation section produces, as bottoms, 39 t/h of water (of which 18 t/h are recycled to the brown oil separation section and 21 t/h are purged from the process) and, as overhead, 90 t/h of ethanol effluent feeding the reaction section.

The reaction section comprises two reaction zones. The first is fed with 75 t/h of the ethanol effluent. The effluent from the first reaction zone is separated into a gas effluent and a liquid effluent. The gas effluent (about 11 t/h) is washed with the 15 t/h of the ethanol effluent not feeding the first reaction zone. The washed gas (1 t/h) mainly comprises hydrogen. The ethanol effluent which has washed the gas effluent, as a mixture with the liquid effluent and the ethanol-acetaldehyde effluent obtained from the ethanol treatment step, feeds the second reaction zone at a total flow rate of 112 t/h.

The reaction effluent obtained from the second reaction zone forms a 112 t/h stream comprising 39% ethanol, 6% acetaldehyde, 28% water and 17% butadiene.

This stream is treated in a flash section at 75° C., producing 33 t/h of a liquid effluent, predominantly comprising water, ethanol and heavy impurities (but no longer containing butadiene), which directly feeds the oil treatment section. The flash section also produces a gaseous effluent which, after compression, feeds a second flash section at 45° C. The liquid and gaseous effluent from the second flash section are sent firstly to a separation step (step C) of the process according to the invention) and secondly to a distillation section.

The distillates from the separation step and from the distillation section, the flow rates of which are respectively 9.5 and 11.5 t/h are sent as a mixture to a drying step, then a cooling and compression section.

The residues from the separation step and from the distillation section, the flow rates of which are respectively 57 and 1 t/h, that no longer contain butadiene, are sent as a mixture to the section for washing/backwashing of the effluents with hydrocarbons.

The mixture sent to a drying step, then a cooling and compression section, containing 90% of butadiene, 7% of light compounds and 3% of acetaldehyde, is then sent to a section for separating 1-butene by extractive distillation which makes it possible to draw off, as overhead, a light gas effluent, mainly comprising ethylene, propylene, 1-butene, trans-2-butene and cis-2-butene gases. The bottom of the extractive distillation column feeds a distillation that makes it possible to separate the extractive distillation solvent, the top of this column, which forms the topped butadiene distillate, feeding a section for separating the oxygenated compounds. Said section for separating the oxygenated compounds makes it possible to extract 0.65 t/h of an oxygenated compounds effluent containing the oxygenated impurities (in the sense that they are undesirable in the purified butadiene effluent), including all of the acetaldehyde, which effluent is then sent to the section for washing/backwashing the effluents with hydrocarbons.

The final distillation section results in the production of an effluent of 18.75 t/h of purified butadiene comprising 99.6% by weight of butadiene.

The mixture sent to the section for washing/backwashing the effluents with hydrocarbons, containing overall 48% of ethanol, 34% of water, 7% of acetaldehyde (the remainder consisting of brown oil impurities), feeds, at an intermediate point, a section for washing/backwashing with hydrocarbons in an effluent treatment step in order to separate the impurities, and in particular the brown oils. This section is fed at the top with a flow rate of recycled water of 18 t/h in order to carry out the backwashing operation. The effluent from this section, representing 104 t/h and comprising 42% of ethanol, 6% of acetaldehyde and 47% of water, feeds an acetaldehyde separation section making it possible to separate an ethanol-acetaldehyde effluent and an ethanol-water effluent. The ethanol-acetaldehyde effluent (23 t/h comprising 56% ethanol and 27% acetaldehyde) feeds the second reaction zone.

The ethanol-water effluent feeds the ethanol-water separation section at an intermediate point, this section moreover being fed at the top with the ethanol feedstock as indicated at the start of the example.

Relative to the process not in accordance, a similar overall butadiene yield is obtained (same flow rate of purified butadiene effluent for the same flow rate of feedstock).

The energy consumption of this scheme in terms of utilities (electricity, gas and steam) expressed in MWh is 138.7 MWh, i.e. a 23% reduction in the consumption of utilities. This saving is partly due to better management of the water and ethanol circuit. The reduction in the flow rate of water circulating (of 21 T) in the process leads to a reduction in consumption as regards the separation operations. The choice of the point of injection of the ethanol feedstock also lightens the workload of the separation operations. Since the ethanol feedstock is not used for washing the reaction effluents, it is no longer treated in the effluent treatment steps. These reductions in flow therefore also have the consequence of reducing the size of the equipment.

The invention claimed is:

1. A process for producing butadiene from an ethanol feedstock comprising at least 80% by weight of ethanol, said process comprising:
    A) converting ethanol in a fraction of the ethanol feedstock into butadiene in at least one reaction section at a pressure between 0.1 and 1.0 MPa and at a temperature between 200° C. and 500° C. in the presence of a catalyst, and producing at least one reaction effluent comprising ethanol, butadiene and impurities, wherein the at least one reaction section is also fed with at least a fraction of an ethanol effluent and/or an ethanol-acetaldehyde effluent that results from step E) of this process;
    B) separating the reaction effluent into at least an ethanol-butadiene effluent, an impurities effluent, and a hydrated butadiene effluent;
    C) separating said ethanol-butadiene effluent into at least a butadiene distillate and a contaminated reactants residue comprising ethanol and acetalehyde;
    D) purifying butadiene in the hydrated butadiene effluent and in the butadiene distillate by the steps comprising:
        i) feeding said hydrated butadiene effluent resulting from step B), as a mixture with said butadiene distillate resulting from step C) and with a stream comprising a solvent to a section for separating the butene with extractive distillation to obtain an overhead light gas effluent comprising butene, and a bottoms comprising a butadiene residue, and distilling said butadiene residue into an overhead butadiene distillate and a bottoms comprising a solvent residue;
        ii) separating oxygenated compounds from the overhead butadiene distillate by extractive distillation with a stream comprising solvent to produce an overhead comprising prepurified butadiene effluent, and a bottoms comprising spent solvent residue, and distilling said spent solvent residue to separate an overhead oxygenated compounds effluent and a bottoms comprising solvent residue; and
        iii) distilling said prepurified butadiene effluent resulting from the separating the oxygenated compounds in D) ii) in a final distillation section to produce an overhead comprising a purified butadiene effluent and a bottoms comprising a 2-butene residue; and
    E) treating in an effluent treatment step at least the contaminated reactants residue resulting from step C) and the oxygenated compounds effluent resulting from step D) ii), to produce at least the ethanol effluent, the ethanol-acetaldehyde effluent, and one or more brown oil effluents.

2. The process according to claim 1, in which said reaction section of said step A) comprises two reaction zones, the first fed with a fraction of said ethanol effluent and a portion of said ethanol feedstock, and the second fed with the effluent from the first reaction zone, with the residual fraction of said ethanol effluent and with a fraction of the ethanol-acetaldehyde effluent resulting from step E) and optionally with a portion of said ethanol feedstock, the ethanol/acetaldehyde molar ration of the inlet of said second reaction zone being between 1 and 5.

3. The process according to claim 2, in which gas-liquid separation is conducted between the two reaction zones in order to separate the effluent from the first reaction section into a gas effluent and a liquid effluent, the liquid effluent feeding the second reaction zone.

4. The process according to claim 1, in which said step B) comprises:
    separating said reaction effluent in a gas-liquid separation section into a liquid effluent comprising said ethanol-butadiene effluent and a gas effluent,
    compressing said gas effluent to give a compressed gas effluent compressed to a pressure between 0.1 and 1.0 MPA, and
    separation said compressed gas effluent in a distillation section into an overhead, said hydrated butadiene effluent and a bottoms comprising said impurities effluent.

5. The process according to claim 4, in which said gas-liquid separation section of said step B) is operated at a temperature between 10° C. and 20° C.

6. The process according to claim 4, in which said gas-liquid separation section of said B) is operated at a temperature between 40° C. and 50° C.

7. The process according to claim 4, in which said impurities effluent resulting from step B) is sent to the effluent treatment step E) as a mixture with the contaminated reactants residue resulting from step C).

8. The process according to claim 1, in which said step B) comprises:
- a first gas-liquid separation section that separates said reaction effluent into a liquid effluent comprising said impurities effluent and a gas effluent, operated at a temperature between 70° C. and 80° C., and a pressure of between 0.1 and 0.3 MPa,
- a compression section that compresses said gas effluent to give a gas effluent compressed to a pressure between 0.1 and 1.0 MPa, and
- a second gas-liquid separation section fed with said compressed gas effluent and that separates, as gas phase, said hydrated butadiene effluent and, as a liquid phase, said ethanol-butadiene effluent, operated at a temperature of between 40° C. and 50° C. and a pressure of between 0.2 and 0.6 MPa.

9. The process according to claim 8, in which said hydrated butadiene effluent resulting from said second gas-liquid separation section is fed to a distillation section that separates from said hydrated butadiene effluent, as bottoms, an oxygenated compounds residue and, as overhead, a hydrated butadiene effluent depleted in oxygenated compounds, said hydrated butadiene effluent depleted in oxygenated compounds then feeding step D) as hydrated butadiene effluent.

10. The process according to claim 9, in which said oxygenated compounds residue feeds said effluent treatment step E) as a mixture with said contaminated reactants residue resulting from step C).

11. The process according to claim 9, in which said hydrated butadiene effluent obtained from said distillation section is fed to a water-washing section comprising at least one gas-liquid washing section fed at the bottom with said hydrated butadiene effluent and at the top with a stream of water, and producing, as overhead, a hydrated butadiene effluent, depleted in oxygenated compounds, that feeds step D) and, as bottoms, a spent water raffinate.

12. The process according to claim 8, in which said hydrated butadiene effluent obtained from said second gas-liquid separation section feeds a water-washing section comprising at least one gas-liquid washing section fed at the bottom with said hydrated butadiene effluent and at the top with a stream of water, and producing, as overhead, a hydrated butadiene effluent, depleted in oxygenated compounds, that feeds step D) and, as bottoms, a spent water raffinate.

13. The process according to claim 1, in which said solvent of said butene separation section is selected from the group consisting of dimethylformamide (DMF), N-methylpyrrolidone and acetonitrile.

14. The process according to claim 1, in which the solvent residue resulting from the butene separation in D) i) and the solvent residue resulting from separation the oxygenated compounds in D) ii) are mixed and purified to obtain purified solvent.

15. The process according to claim 1, in which said step E) comprises at least a washing/backwashing section, a section for distilling light brown oils, a section for distilling heavy brown oils, an acetaldehyde separation section and an ethanol-water separation section.

* * * * *